(12) United States Patent
Aslie

(10) Patent No.: US 9,642,719 B1
(45) Date of Patent: May 9, 2017

(54) SPINAL FUSION SYSTEM FOR OSTEOPOROTIC VERTEBRAE

(71) Applicant: Costello Law Corporation, Sacramento, CA (US)

(72) Inventor: Ardavan M. Aslie, Rocklin, CA (US)

( * ) Notice: Subject to any disclaimer, the term of this patent is extended or adjusted under 35 U.S.C. 154(b) by 274 days.

(21) Appl. No.: 13/671,287

(22) Filed: Nov. 7, 2012

(51) Int. Cl.
*A61B 17/70* (2006.01)
*A61F 2/44* (2006.01)

(52) U.S. Cl.
CPC ........ *A61F 2/4455* (2013.01); *A61B 17/7032* (2013.01)

(58) Field of Classification Search
CPC ............ A61B 17/7032; A61B 17/7037; A61B 17/7041; A61B 17/7002; A61B 17/7004
USPC ...................... 606/250–279, 70, 71, 246–249
See application file for complete search history.

(56) References Cited

U.S. PATENT DOCUMENTS

| | | | |
|---|---|---|---|
| 5,558,674 A * | 9/1996 | Heggeness et al. | 606/278 |
| 5,899,905 A * | 5/1999 | Errico et al. | 606/256 |
| 7,303,563 B2 * | 12/2007 | Poyner et al. | 606/279 |
| 7,892,260 B2 * | 2/2011 | Mahoney et al. | 606/265 |
| 8,025,681 B2 * | 9/2011 | Colleran et al. | 606/257 |
| 2002/0016595 A1 * | 2/2002 | Michelson | 606/73 |
| 2006/0106381 A1 | 5/2006 | Ferree et al. | |
| 2008/0021454 A1 | 1/2008 | Chao et al. | |
| 2009/0105761 A1 | 4/2009 | Robie | |
| 2010/0082067 A1 | 4/2010 | Kondrashov | |
| 2010/0094351 A1 * | 4/2010 | Haggenmaker et al. | 606/286 |
| 2013/0041410 A1 * | 2/2013 | Hestad | A61B 17/7032 606/263 |

FOREIGN PATENT DOCUMENTS

| | | |
|---|---|---|
| EP | 1 502 552 | 2/2005 |
| EP | 2 279 707 | 2/2011 |
| FR | 2 900 561 | 4/2006 |

* cited by examiner

*Primary Examiner* — Eduardo C Robert
*Assistant Examiner* — Tara R Carter
(74) *Attorney, Agent, or Firm* — Costello Law Corporation

(57) ABSTRACT

The invention is a spinal fusion system with fusion rod anchors which do not use staples or screws to achieve securement to a patient's spine. The system relies on a head segment pivotally attached to a base having a channel imparted therein, the channel having an entry and exit opening. The rod anchor is secured with a threadable segment which is threaded through the channel and around an associated vertebra. Multiple rod anchors can be attached to a patient's vertebrae in this manner and a fusion rod is inserted into the multiple anchors and locked down inside the rod anchors with a lock nut.

6 Claims, 13 Drawing Sheets

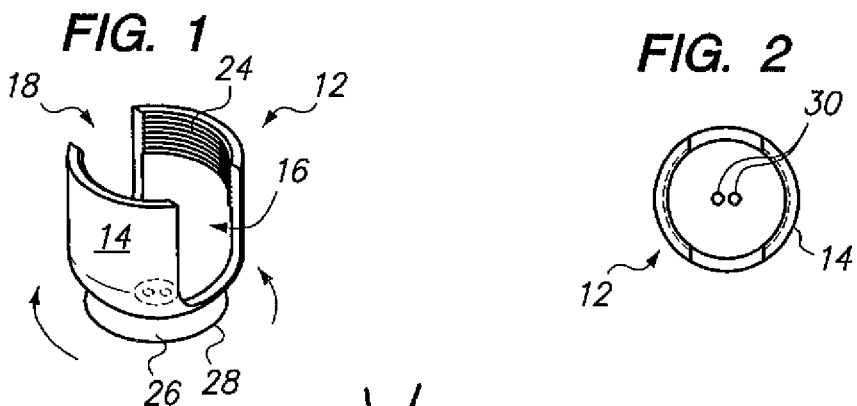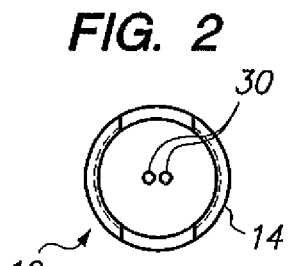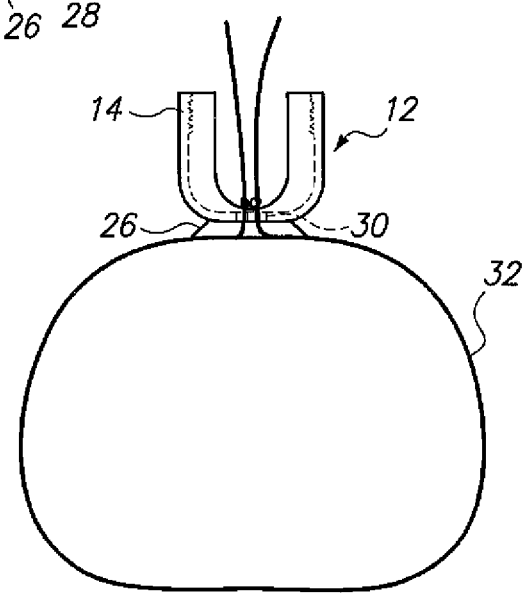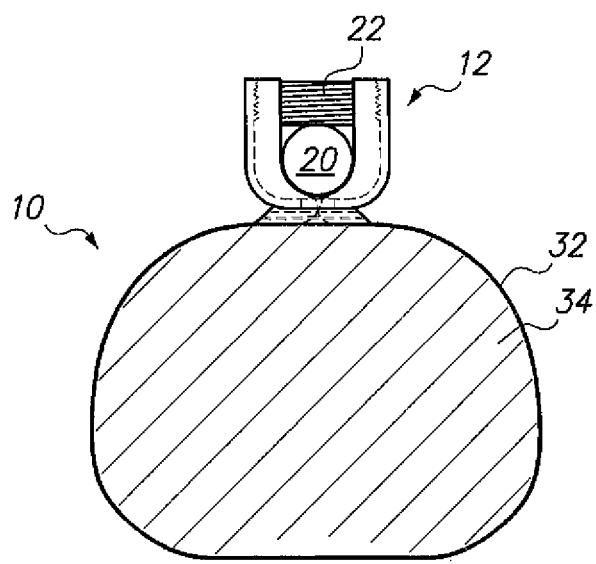

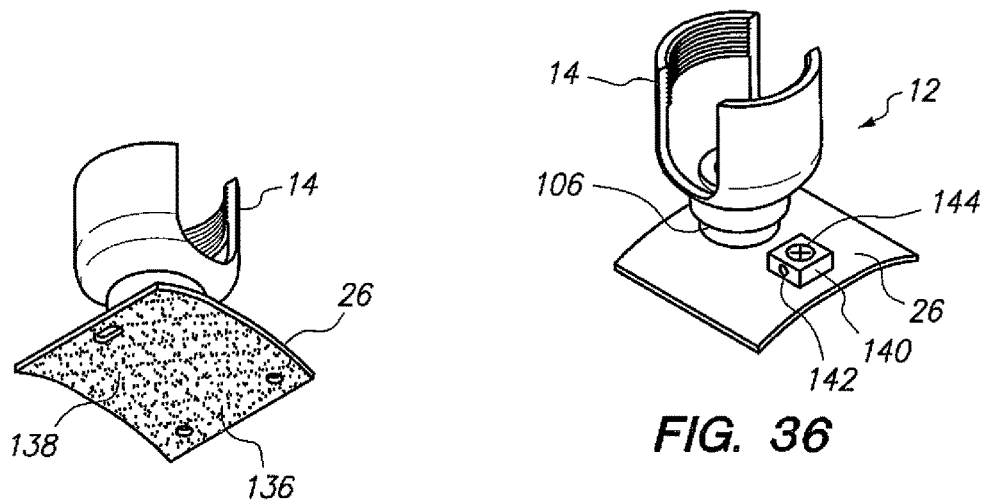
FIG. 35
FIG. 36
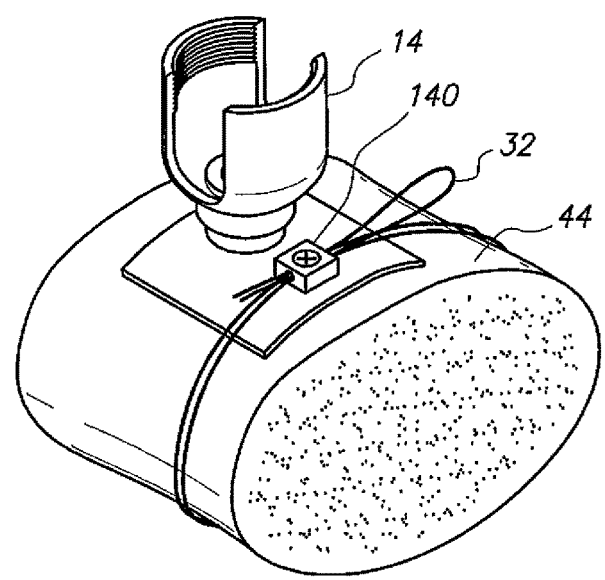
FIG. 37
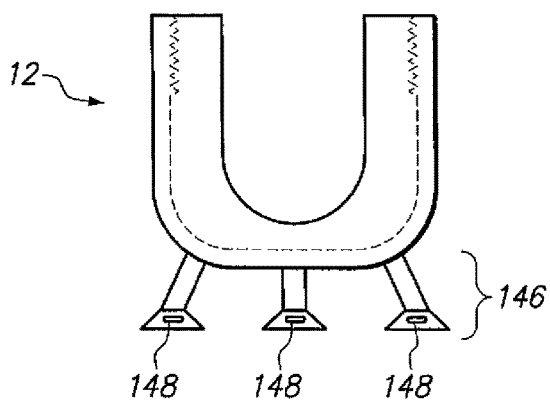
FIG. 38

SPINAL FUSION SYSTEM FOR OSTEOPOROTIC VERTEBRAE

1. RELATED APPLICATIONS

This application claims the benefit, of U.S. provisional patent application Ser. No. 61/594,838, filed on Feb. 3, 2012.

2. TECHNICAL FIELD

This invention relates to spinal appliances and more specifically to a spinal fusion system which is especially applicable to osteoporotic bone.

3. BACKGROUND

Spinal surgery often requires different appliances to be attached to the spine in order to achieve a certain surgical goal. For example, in the area of spinal fusion, the spinal disc is removed between adjacent vertebrae and an appliance is attached which distracts and compresses adjacent vertebrae together. The resulting bone-on-bone contact of adjacent vertebrae results in the vertebrae fusing together, provided that the adjacent vertebrae are held in relative stationary contact over time. A variety of appliances have been devised which attach to the spinal vertebrae to keep them stationary so that fusion can occur.

One type of appliance relates to a system of pedicle screws comprising screws having head segments wherein fusion rods are inserted into the head segments. Exemplary of this type of system are those manufactured by Medtronic, Inc., Synthes Inc., and Depuy Inc. A number of pedicle screws are installed on the spine, appropriate to the number of vertebrae desiring to be fused. The head segments pivot on the screw portion and are aligned so that their open sides are parallel with the vertical axis of the spine and a fusion rod of appropriate length is placed in the heads of adjacent pedicle screws, the rod subsequently being locked down inside the head segment with lock nuts.

The use of pedicle screws to anchor a spinal appliance works well with healthy, young bone; however where the bone has become osteoporotic, as in the case with older patients, the screws often become loose or back out. One solution to this problem has been to attach the fusion rods to the spine using nylon sub-laminar straps. This procedure is described in O'Brien et al., "*Nylon Sublaminar Straps in Segmental Instrumentation for Spinal Disorders*," Clinical Orthopedics and Related Research, Number 203 February 1986 pg. 168. The nylon sub-laminar straps are non-invasive, and can be wrapped around the vertebrae. However, these sub-laminar straps do not attach the fusion rods in a locked-down fashion, and therefore, do not lock the vertebrae in a sufficiently stationary manner. Therefore, the vertebrae cannot be sufficiently distracted and compressed together for proper fusion using these types of sub-laminar straps.

United States Patent Application No. 20090105761 (Robie) represents a system for anchoring adjacent spinal vertebrae without using a screw system. This invention uses a type of strap that is anchored by staples to an inferior vertebral body wherein the strap is further threaded through the spinous process of the superior vertebral body thus tying together two adjacent vertebrae. This patent application does not address the issue of its performance in osteoporotic bone. The dependence of this system on staples may be a drawback, as stapling to a foundation of osteoporotic bone may not result in a long-term anchoring of the strap if the staple eventually works free.

The foregoing reflects the state of the art of which the inventor is aware, and is tendered with a view toward discharging the inventor's acknowledged duty of candor, which may be pertinent to the patentability of the present invention. It is respectfully stipulated, however, that the foregoing discussion does not teach or render obvious, singly or when considered in combination, the inventor's claimed invention.

SUMMARY OF THE INVENTION

The invention is a spinal fusion system for application especially to osteoporotic bone, although its application is not limited as such. The system relies on attaching at least two rod anchors on respective adjacent vertebrae. The rod anchors have head segments adapted for receiving a fusion rod and a base that sits tightly against the vertebral surface. The head segment and base could be one solid piece or could be attached to each other in a rotatable fashion. The base could contact the vertebral surface at a plurality of contact points, such as a base having a plurality of individual legs. The base could also contact the vertebral surface over a larger surface area, such as with a relatively planar, malleable base which would be appropriately shaped to accommodate complex vertebral anatomy.

The base is held tightly against the vertebral surface through the use of flexible threadable segments. The threadable segments can be made of any flexible material that is nonreactive inside the body. Examples of materials which could comprise the threadable segments could be flexible nonreactive materials such: plastics, nylon, carbon fiber, or metal. Exemplary embodiments illustrated herein employ Mersilene® tape or Dyneema® thread as threadable segments which accommodate the requirements of the invention. In addition a "zip-tie" or sublaminar strap system could operate as a threadable segment, provided that these could be tensioned sufficiently to render the rod anchors stationary against the vertebrae.

Once the rod anchors are tied down and the flexible segment is tensioned, the fusion rod can be inserted into the head segment and locked down to distract and compress the adjacent vertebrae so fusion can occur. This system does not rely on screws or staples which require invading the bone surface to obtain a secure hold. Instead, this system's reliance on flexible threadable segments allows the system to be attached to the exterior of the bone which is believed to result in a more reliable and longer lasting fusion system for patients suffering from osteoporosis.

Because this device is capable of attaching to vertebrae rigidly at first and then accepts the fusion rod, it possesses all the capabilities of pedicle screws without their downfall; which downfall is a high failure rate in osteoporotic bone. Pedicle screws rely on cancellous bone in the core of vertebrae for their grip, which is significantly affected in osteoporosis. This invention relies on the outer cortical bone for its grip which is affected a lot less in osteoporosis.

Accordingly, the following objects and advantages of the invention apply:

It is an object of this invention to provide a reliable system for attaching a spinal fusion appliance to osteoporotic bone.

It is another object of this invention to provide a spinal fusion appliance which does not rely on screws, staples, hooks, claws or other bone-invasive means to attach the appliance to the spine in a rigid, stable fashion.

It is still another object of this invention to provide a spinal fusion appliance which does not experience the failure rate of bone anchoring systems (in osteoporotic bone) that depend on screws, staples, hooks, claws or other bone-invasive anchoring means.

Further objects and advantages of the invention will be brought out in the following portions of the specification, wherein the detailed description is for the purpose of fully disclosing the preferred embodiments of the invention, without placing limitations thereon.

BRIEF DESCRIPTION OF THE DRAWINGS

The invention will be more fully understood by reference to the following drawings which are for illustrative purposes only:

FIG. 1 is a perspective view of a first embodiment rod anchor of the inventive spinal fusion system.

FIG. 2 is a plan view of the first embodiment of the rod anchor of the inventive spinal fusion system, showing vertical channels extending through the base of the rod anchor for threading Mersilene® tape.

FIG. 3 is a front view of the rod anchor of FIG. 1 shown with Mersilene® tape suture material threaded through the vertical channels in the base of the anchor.

FIG. 4 is a front view of the inventive spinal fusion system employing the rod anchor of FIG. 1 secured to a patient's vertebrae; this view showing the rod secured with a lock-nut.

FIG. 35 is a bottom view of the base of the eleventh embodiment, showing a textured bottom surface.

FIG. 36 is a perspective view of a twelfth embodiment of the rod anchor, this embodiment employing a lockdown member mounted on a planar base that is separated from the head segment.

FIG. 37 is a perspective view of the twelfth embodiment mounted on a lamina of a vertebra.

FIG. 38 is a side view of a thirteenth embodiment of the rod anchor. This embodiment employs a plurality of legs which attach to the head segment, the legs distributing force through multiple points of contact upon the vertebral surface.

DETAILED DESCRIPTION OF THE PREFERRED EMBODIMENTS

Figure 5:
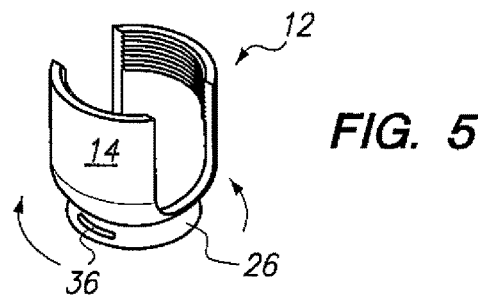
FIG. 5 is a perspective view of a second embodiment rod anchor of the inventive spinal fusion system.

In one exemplary prior art system, fusion rods were anchored with pedicle screws, wherein the pedicle screws had s top head segment adapted for receiving a fusion rod and a lower screw portion pivotally attached to the head segment. The head segment of a pedicle screw had u-shaped aligned entry and exit openings imparted through the sidewalls of the head segment to allow a fusion rod to pass through and be secured within the head segment, using a threaded lock nut. The u-shaped openings provided a rounded bottom for resting the circular fusion rod therein. The head segment of the reference prior art system has a hollow vertical core surrounded by sidewalls, the sidewalls having an interior threaded surface for engaging with the threaded lock nut. The screw portion depending downward from the head segment is driven into the spine of a patient to secure the pedicle screw.

By way of exemplary embodiments, the inventive spinal fusion system for osteoporotic vertebrae allows the securement of rod anchors to a patient's spine without using screws or staples. The head segments may be of a top loading or side loading variety as will be further shown herein. Referring to FIG. 1, a first embodiment of the rod anchor 12 shows that it employs the head segment 14 (in this case a top loading head segment) of the prior art in that it has u-shaped openings 16, 18 for inserting a fusion rod 20. Referring to FIG. 4 and a second embodiment shown in FIG. 9, the fusion rod 20 connects adjacent rod anchors 12 together when they are placed on a patient's spine. The fusion rod 20 is secured with a lock nut 22 and the rod anchor 12 is secured to the spine with Mersilene® tape to form the spinal fusing system 10. The interior sidewall of the rod anchor 12 is threaded 24 to receive the lock nut 22. As further seen in FIG. 2, the head segment 14 of the rod anchor 12 is pivotally attached (see arrows indicating a pivoting motion in FIG. 1) to a base 26 having a planar bottom surface 28, the base 28 of this first embodiment having two vertical channels 30, each having an entry and exit for threading a threadable segment, such as Mersilene® tape 32 and tying the rod anchor 12 securely to the spine. The threadable segment 32, can be a segment cut from a roll of flexible material, such as a roll of Mersilene® tape, or the threadable segment may be a stand-alone flexible appliance that is purpose built for threading into the base 26 and locking down the rod anchor 12 securely. Once the rod anchor is secured, the pivoting head segment 14 can be aligned in the proper direction for attaching the fusion rod 20 as will be further described herein. Referring also to FIG. 3 the Mersilene® tape 32 is shown being threaded through the channels 30 which extend through the bottom of the base. The Mersilene® tape 32 is then tied off so that the knot extends between the two channels 30 shown in FIG. 2 on the inside of the head segment 14. Once, the Mersilene® tape 32 is knotted and secured to a vertebra 34, a fusion rod 20 is inserted in U-shaped openings 16, 18 of the head segment 14, on top of the knotted Mersilene® tape 32, the rod 20 being secured with a threaded lock nut 22 which engages with threads 24 as shown in FIG. 4.

Figure 6:
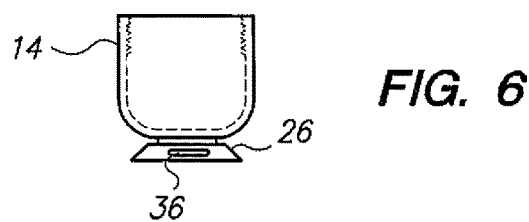
FIG. 6 is a side view of the second embodiment rod anchor of FIG. 5, illustrating a channel opening for threading Mersilene® tape suture material.
Figure 7:
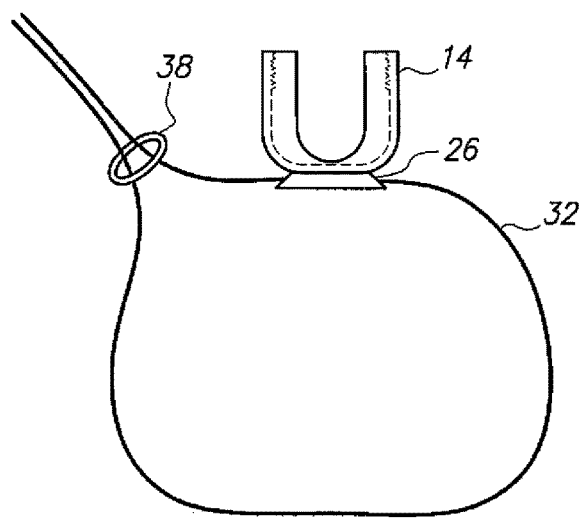
FIG. 7 is a front view of the rod anchor of FIG. 5 shown with Mersilene® tape suture material threaded through the channel opening.
Figure 8:
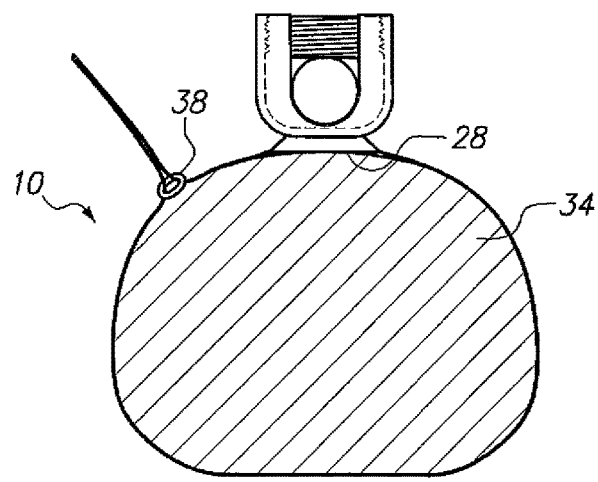
FIG. 8 is a front view of the inventive spinal fusion system employing the rod anchor of FIG. 5 secured to a patient's vertebra.

Referring now to FIGS. 5-11, the second embodiment of the rod anchor 12 is shown. In this embodiment, the head segment 14 of the rod anchor 12 is positioned atop base 26 which has a flattened bottom surface 28, wherein the base has a horizontal through-channel with opening 36 for inserting the Mersilene® tape 32. In FIG. 5, the base 26 is shown with the head segment 14 pivoting (see arrows in FIG. 5) in relation to the base 26. In FIG. 6-8, it is shown that the base 26 includes a channel opening 36 in its side for threading Mersilene® tape 32 which secures the rod anchor 12 to a patient's vertebra 34. In FIG. 7, the threading of the Mersilene® tape 32 through the base 26 is shown with a crimp ring 38, which is used to tension and tie off the tape around the patient's vertebra 34. In FIG. 8, the flat bottom surface 28 of the base 26 is positioned on a patient's vertebra 34 and Mersilene® tape 32 is passed through the channel openings 36 on each side of base 26 and tied off by threading the tape 32 through the crimp ring 38 and knotting it.

Figure 9:
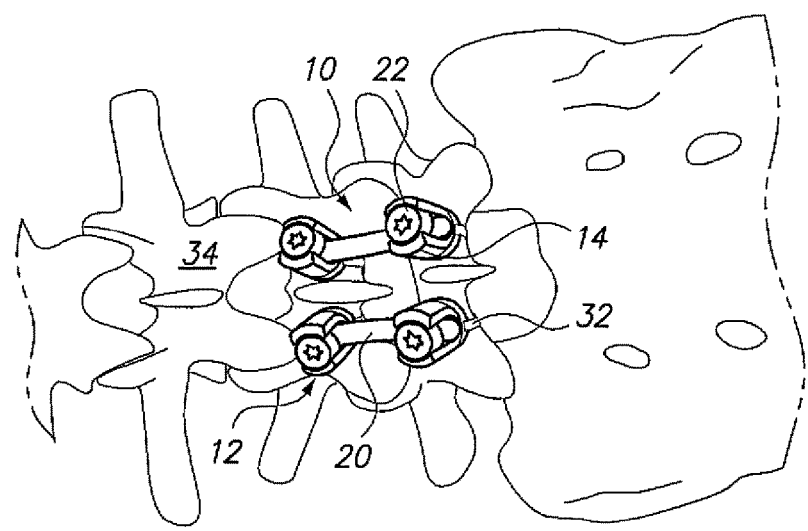
FIG. 9 is a plan view of a section of the spine showing the inventive spinal fusion system attached to the individual vertebra with Mersilene® tape.

When the inventive spinal fusion system 10 is fully assembled upon a patient's vertebrae 34, the assembly appears as that shown in FIG. 9; this view employing rod anchors of the second embodiment as presented in FIGS. 5-8. A section of adjacent vertebrae is shown prepared for fusion by employing the instant invention. As shown, adjacent vertebrae have a rod anchor 12 attached with Mersilene® tape 32 and a fusion rod 20 is positioned in the rod anchors 12. Each rod anchor has a lock nut 22 which locks the rod 20 immovably within the rod anchor 12. When left so immobilized for a period of time by the inventive fusion system 10, the section of spine to which it is applied fuses fully.

Figure 10:
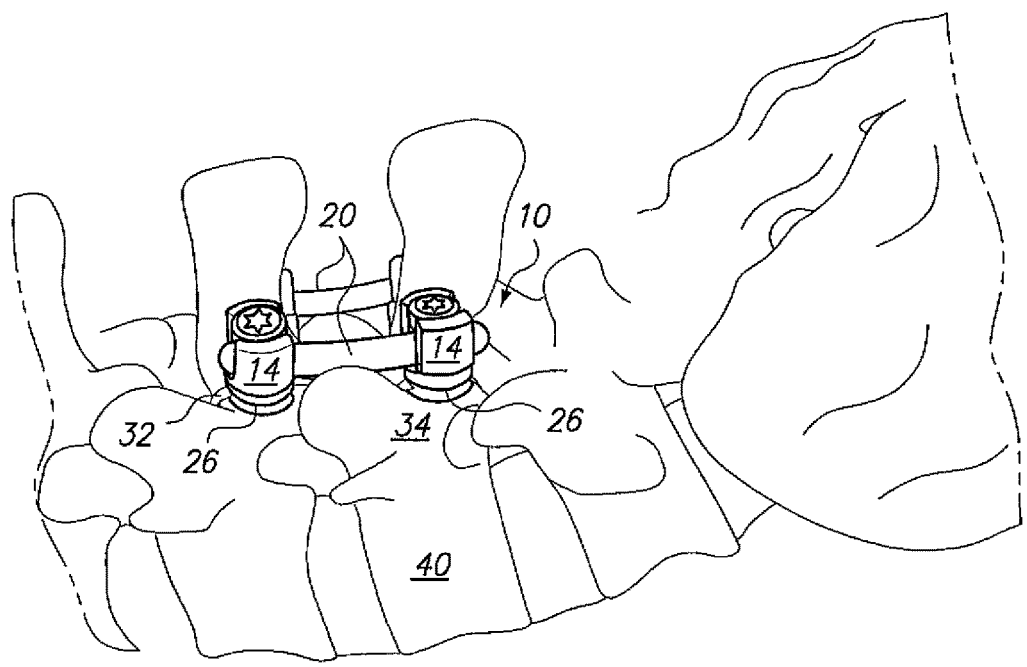
FIG. 10 is a close-up side perspective view of a section of the spine showing the inventive spinal fusion system attached to individual vertebra with Mersilene® tape.
Figure 11:
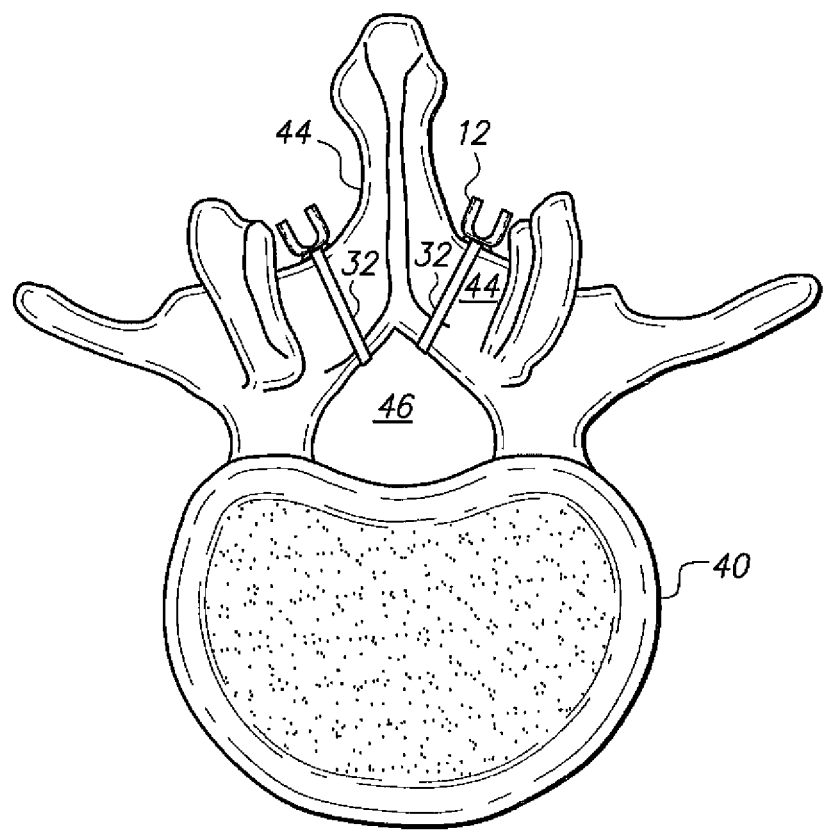
FIG. 11 is a cross-section of lumbar vertebra showing the rod anchors attached to the vertebra with Mersilene® tape.

FIG. 10 is a close-up side view of the assembled system 10. In this view the inventive spinal fusion system 10 is shown attached to a section of lumbar vertebrae 40. The rod anchors 12 (as represented by the second embodiment shown in FIGS. 5-9) are positioned on the lamina, which offers a relatively flattened surface for placing the flat bottom surface 28 of the base 26. The Mersilene® tape 32 is looped through the rod anchor 12 in the manner previously described and then looped around the lamina and through the spinal foramen and tied off, thus securing the rod anchor 12 to the lumbar vertebrae 40. In FIG. 11, this shows a cross section through a lumbar vertebra 40 showing the Mersilene® tape 32 looping around the lamina 44 and through the spinal foramen 46 to ultimately secure the rod anchors 12 to the lumbar vertebra.

Figure 12:
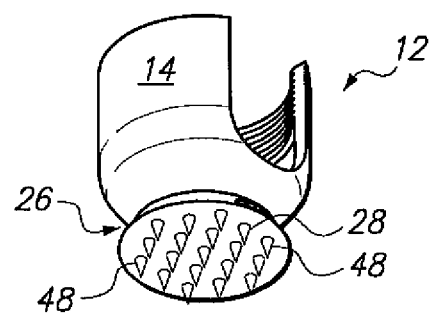
FIG. 12 is a bottom perspective view of a third embodiment of the rod anchor showing a plurality of anchor spikes located on the planar bottom surface of the base of the rod anchor.

FIG. 12 introduces a third embodiment of the rod anchor 12. This embodiment has a plurality of anchor points 48 protruding from the planar bottom surface 28 of the base 26 of the rod anchor 12. These anchor points 48 can take the form of a plurality of pointed spikes which "bite" into the surface of the vertebra, thus aiding in the attachment of the rod anchor 12 solidly to the vertebra. The Mersilene® tape is then threaded through the channel in the base 26 of the rod anchor 12 in the same ways as described previously herein. During surgery, the surgeon would set the base 26 on the vertebra 34, thus making contact between the anchor points 48 and the spinal surface. The surgeon could then gently tap the top of the head segment 14 of the rod anchor 12, thus lightly driving the anchor points 48 into the surface of the vertebra until the bottom 28 of the base 26 is flush with the vertebral surface. The rod anchor 12 could then be attached to the vertebra with Mersilene® tape as previously described and shown.

Figure 13:
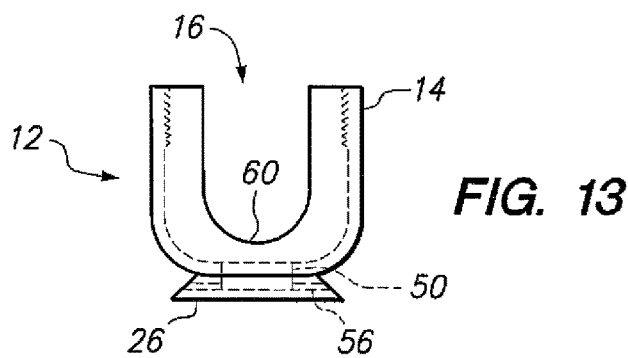
FIG. 13 is a front view of a fourth embodiment of the rod anchor having a cavity in the base of the rod anchor for inserting a compression member.

FIG. 13 illustrates a further fourth embodiment of the rod anchor 12 which has a modification to the base 26 that involves imparting a cavity 50 (shown in phantom) into the middle of the base 26. The cavity 50 is preferably cylindrical and is intended to receive a cylindrical compression member 51 therein. The compression member 51 includes a top surface 53 which contacts the fusion rod. The compression member 51 is intended to compress the Mersilene® tape 32 resting on the bottom of the cavity 50 and hold it fast.

Figure 14:
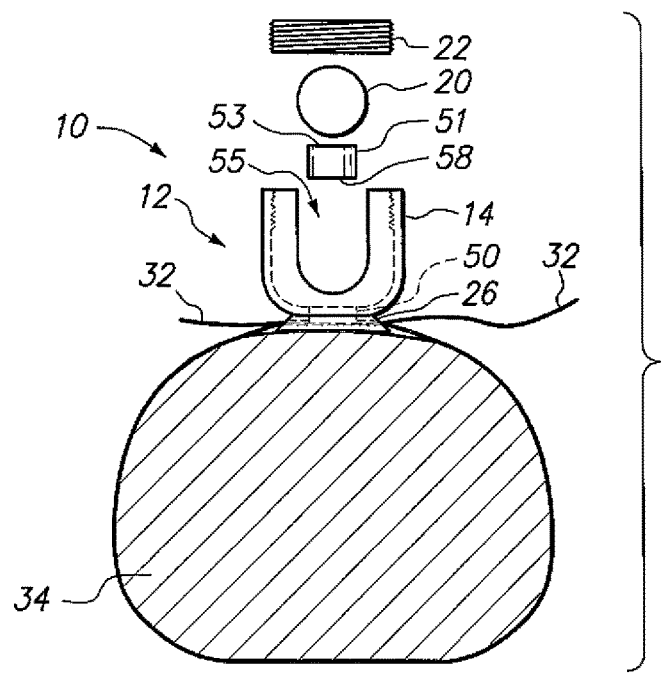
FIG. 14 is a partially exploded front view of the rod anchor introduced in FIG. 13 being positioned on the vertebra and showing the compression member, fusion rod and locknut.

FIG. 14 shows the system 10 employing the rod anchor 12 introduced in FIG. 13. The compression member 51 is shown descending through the hollow vertical core 52 of the head segment 14 to eventually rest in the cavity 50, which is substantially aligned with vertical core 52. Here it is shown how the Mersilene® tape 32 is threaded through the openings 36 (not visible in this view) and interior channel 56 (shown in phantom) of the base 26, the channel 56 opens into the cavity 50. The Mersilene® tape 32 crosses the cavity 50 and when the compression member 51 is inserted into the cavity 50 it rests directly on the tape 32.

Figure 15:
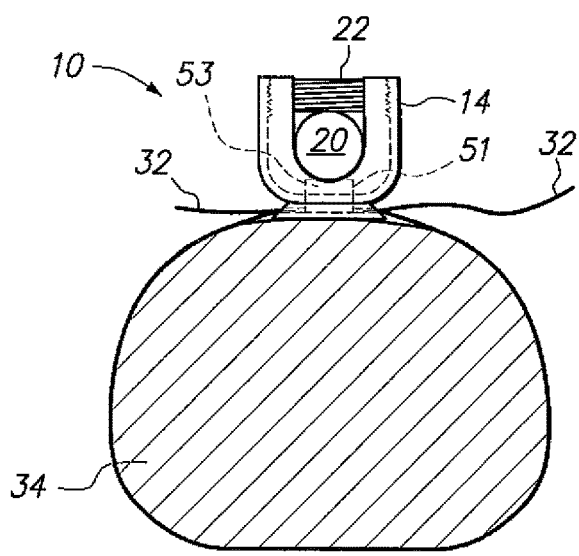
FIG. 15 is a front view of the assembled system incorporating the fourth embodiment of the rod anchor shown positioned on the vertebra.

In FIG. 15, the complete assembly of the invention is shown for the embodiment introduced in FIG. 13. The fusion rod 20 rests on the top surface 53 of the compression member 51. A lock nut 22 exerts downward force upon the fusion rod 20 and compression member 51. The downward force of the rod 20 on the top surface 53 applies the bottom surface 58 of the compression member 51 tightly against the Mersilene® tape 32 lying on the bottom of the cavity 50. This downward applied force locks the Mersilene® tape 32 into an immovable position. Although it is not shown, the Mersilene® tape 32 would be tensioned with a mechanical tensioner prior to locking down the compression member 51 against the Mersilene® tape 32. The lock nut 22 is threaded into the rod anchor 12 until it contacts the fusion rod 20 and applies downward pressure upon the fusion rod 20. The fusion rod 20 is tightened downward until it rests tightly against the lowest point 60 of U-shaped openings 16, 18. At this point, the fusion rod 20 applies massive downward pressure against the compression member 51, which likewise exerts massive pressure on the bottom surface 58 of compression member 51. Beneath bottom surface 58 is the Mersilene® tape 32 which is compressed and held fast between the bottom of cavity 50 and bottom surface 58. This pressure on the Mersilene tape 32 is sufficient to render it immovable with the cavity 50

Figure 16:
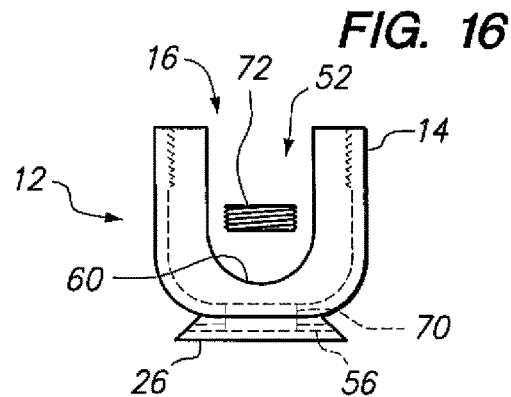
FIG. 16 is a partially exploded front view of a fifth embodiment of the rod anchor; this embodiment having a threaded cavity in its base and a threaded cavity lock nut.
Figure 17:
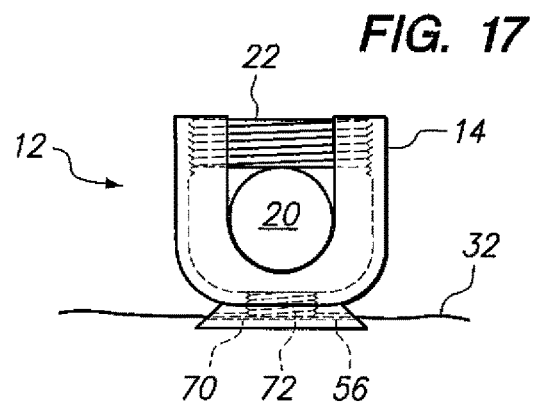
FIG. 17 is a front view of the assembled system incorporating the fifth embodiment of the rod anchor introduced in FIG. 16.

In FIG. 16 an exploded view of the system employing a fifth embodiment of the rod anchor 12 is shown, this embodiment employing a central cavity 70 with threaded side walls; the cavity 70 extending into the base 26 and aligning with the hollow vertical core 52 of the head segment 14. Referring also to FIG. 17, the threaded cavity 70 receives a secondary lock nut 72 which is threaded into the cavity 70 until it contacts the Mersilene® tape 32 lying on the bottom of cavity 70. The Mersilene® tape 32 extends through horizontal channels 56 in base 26 and across the bottom of cavity 70. By bottoming the secondary lock nut tightly against Mersilene® tape 32, the tape can be held immovably. Therefore the Mersilene® tape 32 can be wrapped around the vertebra and then tightened with a tensioning tool and held fast in the cavity 70 by the secondary lock nut 72.

Figure 18:
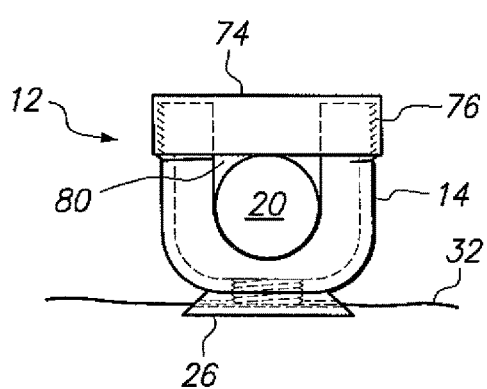
FIG. 18 is a front view of a sixth embodiment of the rod anchor, this embodiment employing a threaded cap.
Figure 19:
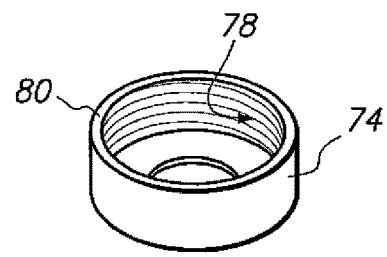
FIG. 19 is a bottom perspective view of the cap introduced in FIG. 18.
Figure 20:
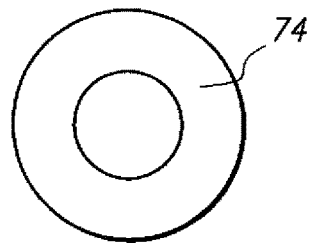
FIG. 20 is a top perspective view of the cap introduced in FIG. 18.

FIG. 18 shows a sixth embodiment of the rod anchor 12 which employs a threaded cap 74 which engages with threads 76 on the exterior sidewalls of head segment 14. The cap 74 is an alternative to a lock nut 22 which has been shown in the previous drawings. FIGS. 19 and 20 show the cap 74. Cap 74 has threads 78 along its interior side wall which engage with the threads 76 on the exterior sidewall of the head segment 14. Cap 74 has a lower circumferential bottom edge 80. As cap 74 is screwed down, bottom edge 80 contacts fusion rod 20 and tightens down against fusion rod, thus holding it in place, as shown in FIG. 18. Alternatively, instead of being screwed down, cap 74 could be press fit upon head segment by means well known in the art.

Figure 21:
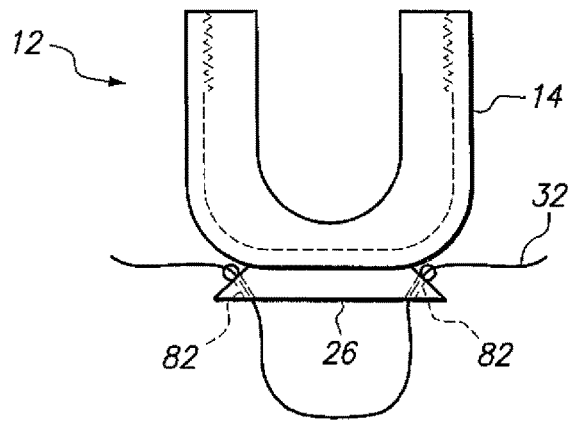
FIG. 21 is a front view of a seventh embodiment of the rod anchor shown with a base having offset vertical channels for threading Mersilene® tape.

FIG. 21 shows a seventh embodiment of the rod anchor 12 with offset vertical channels 82 (shown in phantom) imparted laterally in the base 26. As shown the Mersilene® tape 32 is threaded through the vertical channels 82 and can be tied off or crimped by means already described herein.

Figure 22:
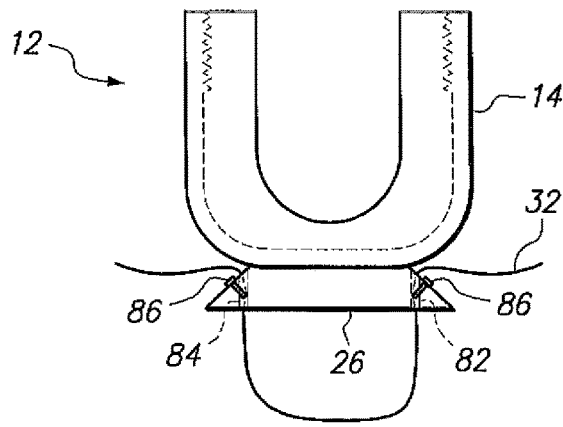
FIG. 22 is a front view of an eighth embodiment of the rod anchor shown with a base having vertical channels and lock-down screws threaded into the base and intruding into the channels to secure the Mersilene® tape threaded into the channels.

FIG. 22 shows an eighth embodiment of the rod anchor 12, again with lateral vertical channels 84 (shown in phantom) imparted in the base 26. Mersilene® tape 32 is threaded through the channels 84. In this embodiment, however, lock screws 86 are threaded into the base 26 so that they protrudingly engage into the vertical channels 84 so as to be tightened against the Mersilene® tape 32, thus holding the tape fast, as shown.

Figure 23:
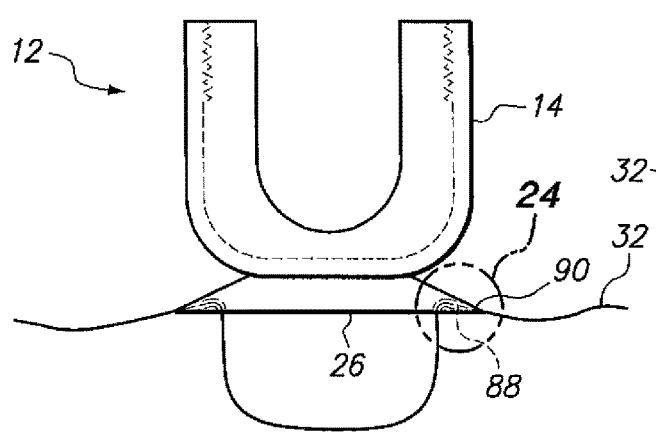
FIG. 23 is a front view of a ninth embodiment of the rod anchor shown with the base having channels which end in a crimping edge for securing the Mersilene® tape threaded into the channels.
Figure 24:
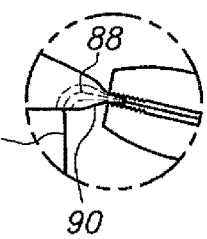
FIG. 24 is a close-up view of the crimping edge introduced in FIG. 23.

FIG. 23 shows a ninth embodiment of the rod anchor 12, this embodiment employing channels 88 in the base 26 which taper outward toward the edge 90 of the base 26, thus allowing the Mersilene® tape to be threaded and exit at the edges 90 of the base 26. Where the channels 88 end, the metallic base material is made sufficiently malleable so that the edges 90 of the base 26 can be crimped together, thus immovably trapping the Mersilene® tape 32 in a tightened relation. With this embodiment, one side of the Mersilene® tape 32 can be crimped at one edge 90 while the Mersilene® tape 32 is pulled tight at the other edge 90 of the base 26 and crimped. FIG. 24 shows a close-up of the crimping edge 90 of the base showing the thread 32 entering and exiting the channel 88 at the crimp edge 90.

Figure 25:
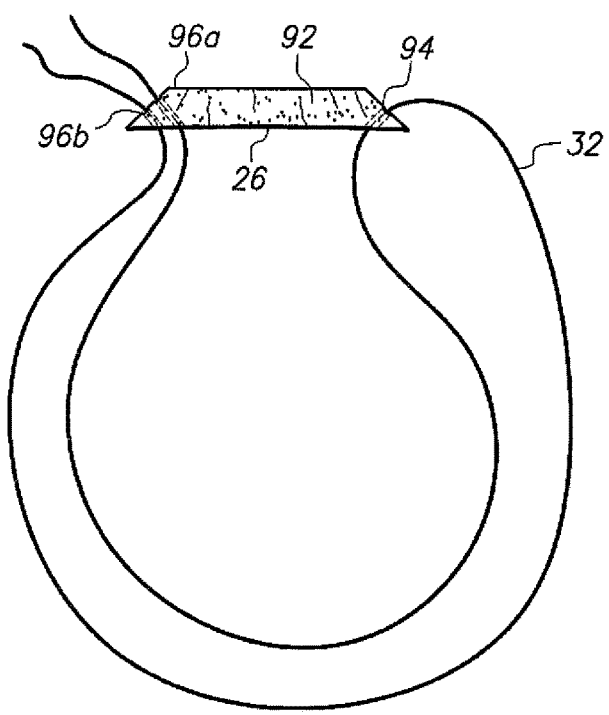
FIG. 25 is a front view of a base embodiment wherein a plurality of through-channels are arranged in the base to allow the Mersilene® tape to be threaded and tied off as shown.

FIG. 25 illustrates another embodiment of the base 26 of the invention. The base 26 is constructed from a malleable material, such as a malleable metal which can be formed to fit a particular vertebral surface. This view also shows another method of tying off the base using the Mersilene® tape 32. A single channel 94 occupies one side of the base 26 into which the tape 32 is threaded and the opposite side of the base included two channels 96a, 96b for threading the two separate ends of the tape 32 through, and tying the whole arrangement off.

Figure 26:
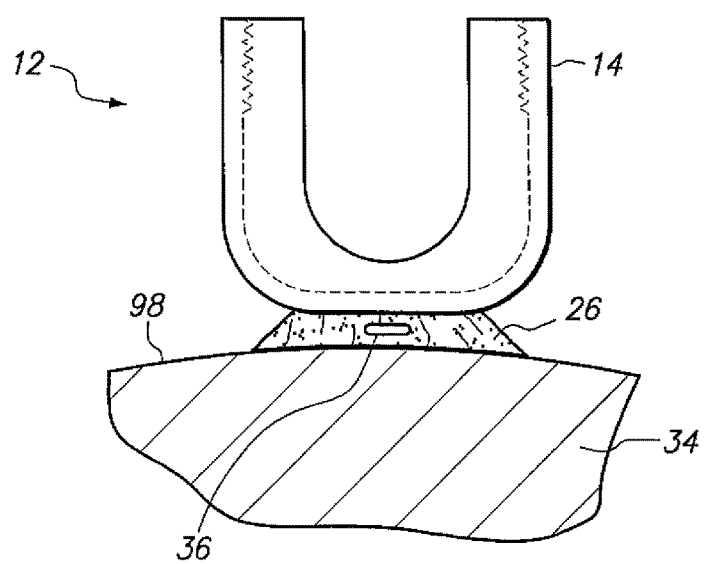
FIG. 26 is a side view of a tenth embodiment of the rod anchor, this embodiment presenting a base that is malleable.

FIG. 26 illustrates a tenth embodiment of the rod anchor 12 incorporating a malleable base 26; the malleable base 26 being formable to the irregular surface 98 of a vertebra 34. By form-fitting to a vertebral surface 98, this embodiment achieves better purchase upon the vertebra. The malleable base 26 retains the channel and channel opening 36 for threading the Mersilene® tape, as described in prior embodiments. The form fitting function is achieved by the surgeon using tools to form the base 26, as needed, to better fit upon the various surface anomalies encountered on the surface 98 of the vertebra 34.

Figure 27:
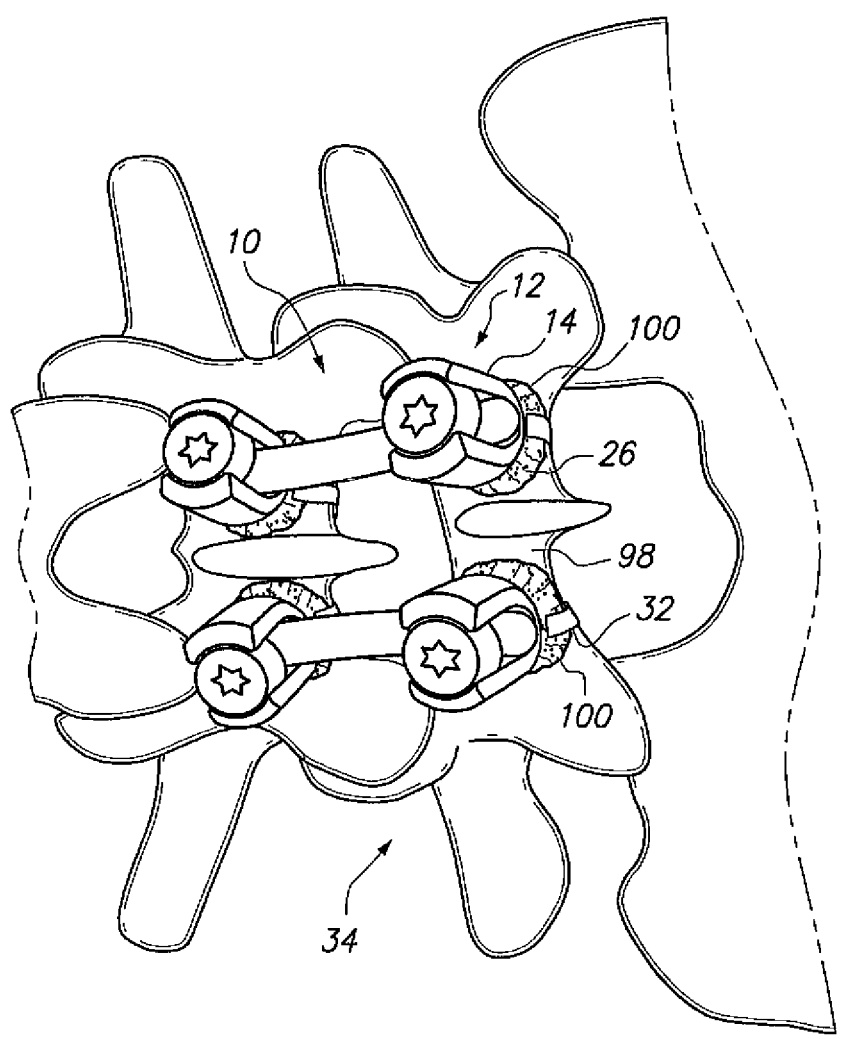
FIG. 27 is an elevated perspective view of the rod anchor embodiment introduced in FIG. 26 incorporated into a spinal fusion system and mounted to a section of lumbar vertebrae.

FIG. 27 shows a plan view of the system 10 applying the rod anchor embodiment 12 introduced in FIG. 26 and mounted on a vertebra 34. The various shapings 100 of the malleable bases 26 as determined by the surgeon are readily apparent to best mate to the changing surfaces 98 of the vertebra 34.

Figure 28:
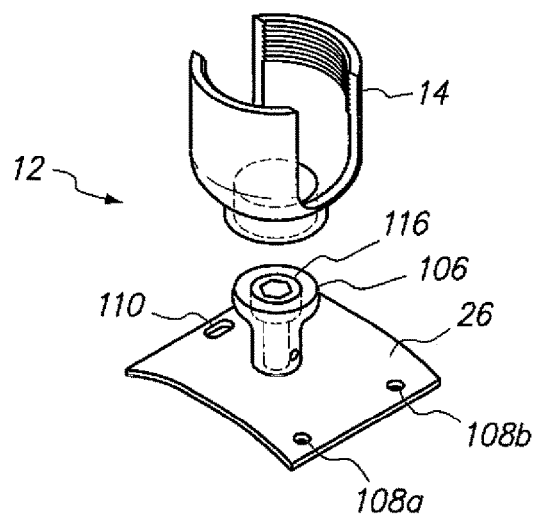
FIG. 28 is a perspective view of an eleventh embodiment of the rod anchor, this embodiment comprising a male coupling member that locks down a threadable segment and couples to a head segment.
Figure 29:
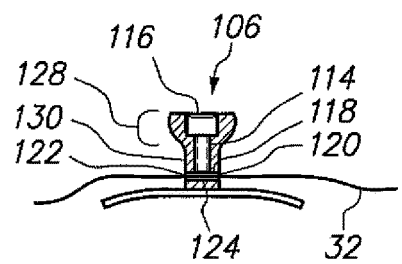
FIG. 29 is a close-up cutaway view of the male coupling member of the eleventh embodiment.

FIG. 28 shows an eleventh embodiment of the rod anchor 12 which employs a malleable base 26 and a separate head segment 14 which can be coupled upon the base 26 via a male coupling member 106 attached to the base 26. The base represented here is planar, square in shape, and has two through-holes 108a, 108b near one side of the base 26 and a third through-hole 110 located at an opposite side of the base from the first two through-holes. While the base 26 shown here is square, the shape of the base can differ to meet the needs of the surgical application; also the arrangement of the through-holes may also vary. The base and remainder of this embodiment, is preferably made of titanium or any other solid, bio-compatible material. The base can be malleable in quality so it can easily be worked into a preferred shape by a surgeon using pliers and other tools know in the art. The male coupling member 106 protrudes upward from the top surface 112 of the base 26, the coupling member 106 here shown as being centered on the base; however it can be arranged in an off-set location on the base, if desired. FIG. 29 shows how male coupling member 106 has a threaded center 114 which engages a threaded lock screw 116, here being represented by a hex screw. The lock screw 116 protrudingly engages into a channel 118 extending transversely through the body of male coupling member 106, the channel 118 having two opposite openings 120, 122. In channel 118 is threaded a threadable segment 32 comprised of Mersilene® tape or Dyneema® thread (an additional example of a threadable segment). The end 124 of the lock screw 116 protrudes into the channel 118 a length sufficient to compress the threadable segment 32 against the walls of the channel 118 and hold it fast.

Figure 30A:
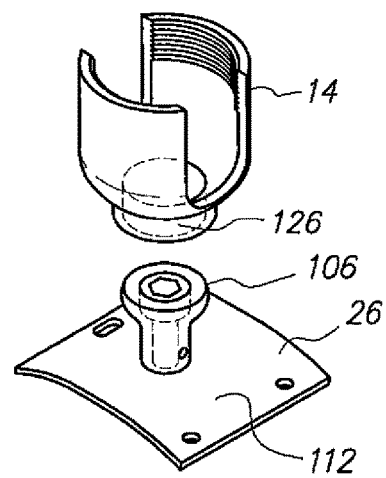
FIG. 30A is a perspective view of the eleventh embodiment showing the head segment detached from the male coupling member.
Figure 30B:
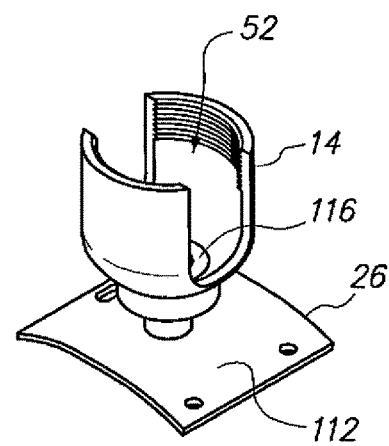
FIG. 30B is a perspective view of the eleventh embodiment showing the head segment attached to the male coupling member.
Figure 31:
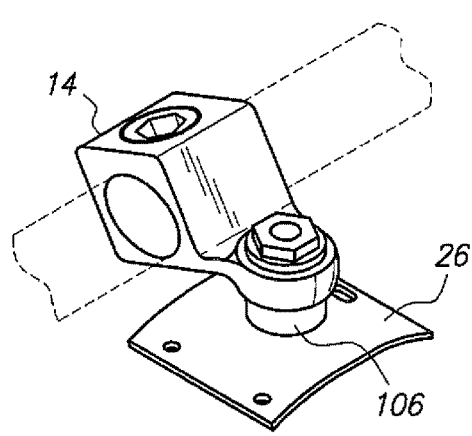
FIG. 31 is a perspective view of the eleventh embodiment shown with a side-loading head segment.

FIGS. 30A and 30B show a head segment 14 being coupled to the male coupling member 106 and base 26 of the eleventh embodiment. The head segment 14 has a cavity 126, (female portion) into which is inserted the male coupling member 106. The head segment 14 is then depressed down upon the male coupling member 106 until it snaps into place upon the male coupling member 106. In one permutation, the "snap" engagement is accomplished by the male coupling member 106 engaging with an expandable ring. The male coupling member 106 comprises a wide shoulder section 128 relative to a narrowed circumference beneath the shoulder section. The head segment 14 has an expanding ring (not shown) seated within cavity 126, which expands over the shoulder section 128 of the male coupling member 106 and then the ring compresses when pushed farther down to meet the narrowed circumference 130 of the male coupling member 106. Once the ring is compressed over the narrowed circumference, the head segment 14 remains tightly coupled to the male coupling member 106, but pivots, as already noted in prior embodiments. The advantage of presenting the eleventh embodiment with the head segment 14 detached is that the threading of the threadable segment through channel 118 of the male coupling member 106 is less obstructed with the head segment 14 detached. However, the eleventh embodiment could be presented with the head segment 14 already attached, prior to mounting on the lamina wherein the head segment 14 would seat high enough on male coupling member so as not to obstruct the channel 118. The head segment 14 which accepts a top-loading fusion rod 20 has a vertical core 52 which allows the top of the lock screw 116 to be accessed. Alternately, a side-loading head segment 14 could be adapted to snap fit onto the male coupling member 106 as shown in FIG. 31. While other embodiments disclosed herein could also be modified to accept a side-loading head segment, the eleventh embodiment's snap fit feature allows a surgeon to select whether to use a top-loading or a side-loading head segment for a particular application.

Figure 32:
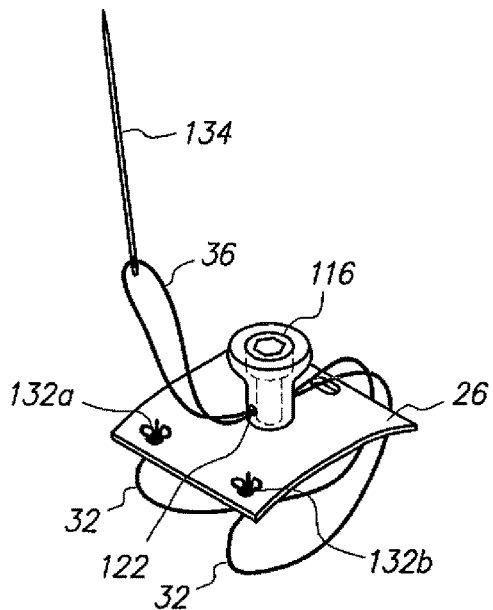
FIG. 32 is a perspective view of the base and male coupling member of the eleventh embodiment shown with a threadable segment attached.
Figure 33A:
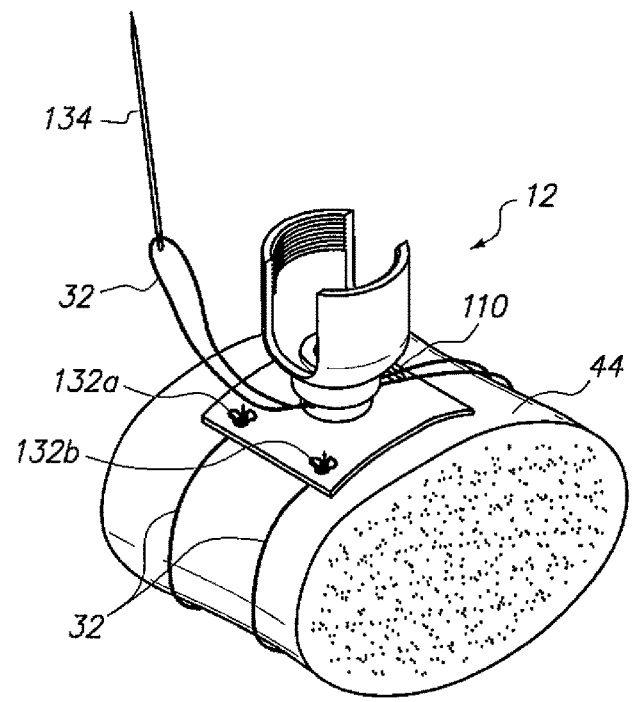
FIG. 33A is a side elevated perspective view of the rod anchor of the eleventh embodiment mounted upon the lamina of a vertebra, having the threadable segment passing through a channel of the male coupling member, the threadable segment being secured at its end with knots.
Figure 33B:
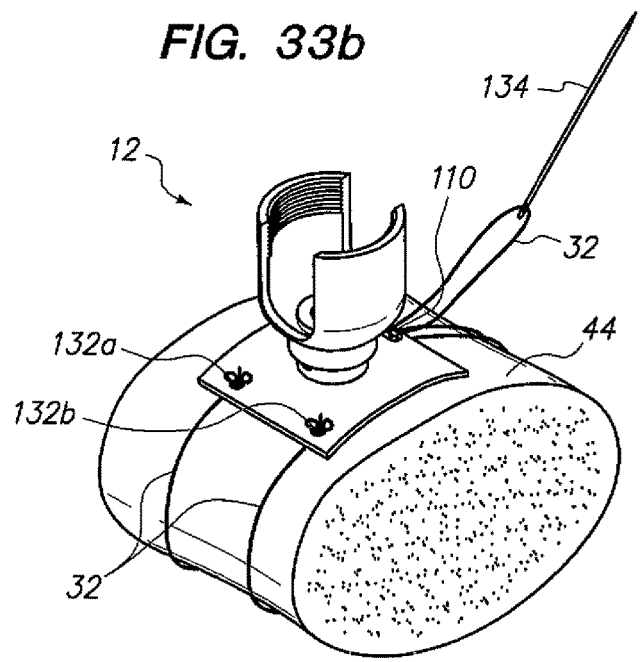
FIG. 33B is a side elevated perspective view of the rod anchor of the eleventh embodiment mounted upon the lamina of a vertebra, having the threadable segment passing through a third through-hole located in the base.

FIG. 32 shows the base 26 and male coupling member 106 prepared for surgery, wherein the ends 132a, 132b of the threadable segment 32 are knotted to prevent them from slipping through the through-holes 108a, 108b as shown. A needle 134 is threaded along the threadable segment 32 which serves to guide the threadable segment 32 around the lamina 44 and through the channel 118 located in the male coupling member 106. FIG. 33a shows the needle having passed through channel 118 after completing the circuit around the lamina 44, the lamina being shown in cutaway. Ends 132a and 132b of threadable segment 32 are knotted and held fast in holes 108a, 108b. The threadable segment 32 is subjected to a tensioning device (not shown), and tensioned to a level of. Once the proper tension is reached, the lock screw 116 is tightened upon the threadable segment 32 located in the channel 118, thus securing the eleventh embodiment immovably on the lamina 44. Any excess portion of the threadable segment 32 is then cut and tied off. Alternately, the threadable segment can be passed through the additional through-hole 110 prior to threading through channel 118 and tightening down as shown in FIG. 33b.

Figure 34:
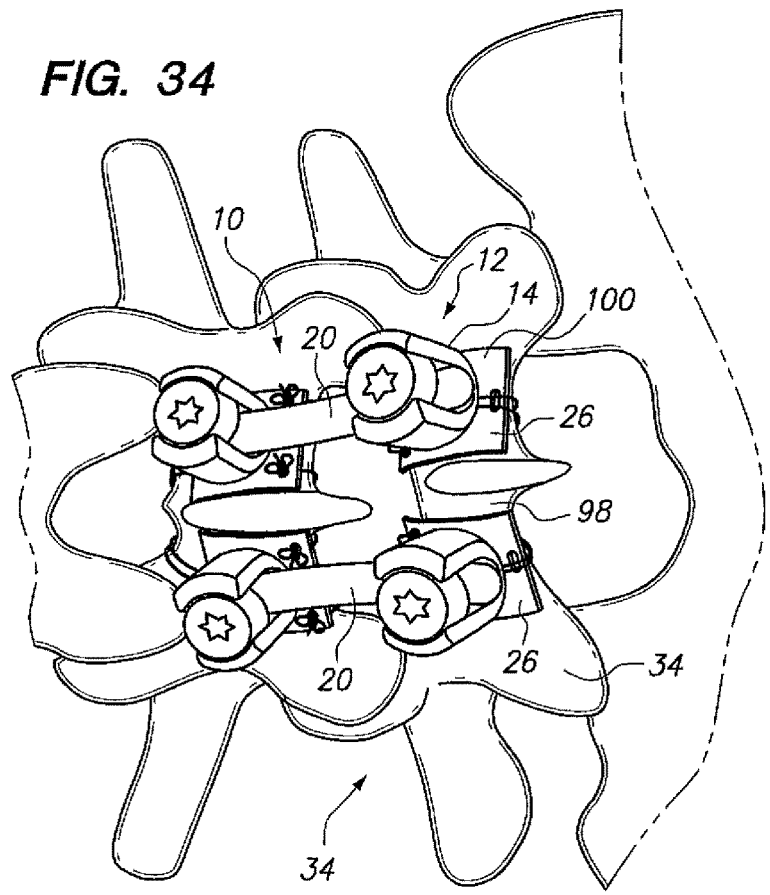
FIG. 34 is a plan view of rod anchors of the eleventh embodiment mounted on a section of vertebra as part of a fusion system including fusion rods loaded into top-loading head segments.

FIG. 34 is a plan view of a fusion system 10 employing the eleventh embodiment mounted on a section of vertebra 34, including fusion rods 20 loaded into top-loading head segments 14. The various shapings 100 of the malleable bases 26 as determined by the surgeon are readily apparent to best mate to the changing surfaces 98 of the vertebra 34.

To further aid in holding fast to a laminar surface, FIG. 35 shows the bottom surface 136 of the base of the eleventh embodiment. The bottom surface preferably has a roughened texture 138 to enhance grip when placed upon the laminar surface.

FIG. 36 introduces yet a twelfth embodiment of the rod anchor 12, wherein the base 26 is similarly planar as with the eleventh embodiment, yet the head segment 14 and coupling member 106 are separate from a lockdown member 140 which secures the threadable segment 32. The base 26, having a malleable quality, can be formed to the lamina 44 as already described. The separate lockdown member 140 has a channel 142 for passing the threadable segment 32 after threading it around the lamina 44. A lock screw 144 of the lockdown member 140 protrudingly engages into the channel 142 for tightening the threadable segment 32 against the walls of the channel. A tensioning device (not shown) can be used to achieve the appropriate tension on the threadable segment to keep the rod anchor 12 immovably attached to the lamina 44. Head segment 14 is adjacent to the lockdown member 140 and pivots upon the coupling member 106. This embodiment has the advantage of not having to tie knots in through-holes as with the eleventh embodiment, as the threadable segment 32 is completely secured by the lockdown member 140, as both ends of the threadable segment 32 thread through the channel 142 from opposite directions after being threaded around the lamina 44 as shown in FIG. 37. Also, the separate lockdown member 140 is unobstructed by the head segment 14 in this embodiment, which allows for unobstructed threading of the threadable segment 32.

FIG. 38 represents a thirteenth embodiment of the rod anchor 12, shown with a three-footed base 146, wherein each foot includes a channel with a channel opening 1484 defining an entry or exit for securing each leg with a threadable segment.

Finally, although the description above contains much specificity, this should not be construed as limiting the scope of the invention, but as merely providing illustrations of some of the presently preferred embodiments of this invention. This invention may be altered and rearranged in numerous ways by one skilled in the art without departing from the coverage of any patent claims, which are supported by this specification.

The invention claimed is:

1. An attachment device for securing to a vertebra, the device comprising:

a head segment with sidewalls surrounding a hollow vertical core, said sidewalls having aligned vertical openings;

a base comprising a malleable material, said base being pivotally coupled to said head segment, said base including at least one channel imparted through said base, said at least one channel having an entry opening and an exit opening; and a flexible threadable segment, said flexible threadable segment being flexibly threadable through said at least one channel, said flexible threadable segment passing through both said entry and exit openings of said at least one channel said flexible threadable segment being configured to non-invasively secure said rod anchor to a surface of a vertebra wherein a tensioning of said flexible threadable segment brings a bottom surface of said base into tensioned contact against a surface of a vertebra.

2. An attachment device for securing to a vertebra, the device comprising:

a head segment;

a base comprising a planar bottom surface, said base further comprising at least one channel imparted through said base;

a coupling member attached to said base, said head segment for being pivotally coupled to said coupling member;

said coupling member further comprising at least one channel imparted transversely through said coupling member, said coupling member further comprising a lock screw protrudingly engaging into said at least one channel imparted transversely through said coupling member; and a threadable segment, said threadable segment being threadable through said at least one channel imparted transversely through said coupling member, said threadable segment passing through said at least one channel imparted transversely through said coupling member, said threadable segment further passing through said at least one channel imparted through said base, said threadable segment being configured to thread around a vertebra and bring said base into tensioned contact with a vertebra.

3. An attachment device for securing to a vertebra, the device comprising:

a head segment, said head segment further comprising a female coupling cavity;

a base comprising a planar bottom surface, said base including at least one channel imparted vertically through said base, said at least one channel having an entry opening and an exit opening;

a male coupling member, said male coupling member being approximately centered upon said base, said male coupling member engaging with said female coupling cavity to pivotally couple said head segment to said male coupling member; and a flexible threadable segment, said flexible threadable segment being flexibly threadable through said at least one channel imparted vertically through said base, said flexible threadable segment passing through both said entry and exit openings of said at least one channel imparted vertically through said base, said flexible threadable segment being configured to non-invasively secure said rod anchor to a surface of a vertebra wherein a tensioning of said flexible threadable segment brings a bottom surface of said base into tensioned contact against a surface of a vertebra.

4. The attachment device as recited in claim 3, wherein said male coupling member further comprises a channel extending transversely through said male coupling member, said channel extending transversely through said male coupling member receiving said flexible threadable segment therein, said male coupling member further comprising a lock screw, wherein an end of said lock screw protrudes into said channel extending transversely through said male coupling member, said lock screw protruding a length sufficient to compress said flexible threadable segment against a wall of said channel extending transversely through said male coupling member.

5. An attachment device for securing to a vertebra, the device comprising:

a head segment;

a base comprising a planar bottom surface, said base further comprising first and second through-holes adjacent a first edge of said base, said base further comprising a third through-hole adjacent a second edge of said base, said second edge of said base being located opposite said first edge of said base;

a coupling member attached to said base, said head segment for being pivotally coupled to said coupling member;

said coupling member further comprising at least one channel imparted transversely through said coupling member, said coupling member further comprising a lock screw protrudingly engaging into said at least one channel imparted transversely through said coupling member; and a threadable segment, said threadable segment being configured to be threadable through said first and second through-holes adjacent said first edge of said base, said threadable segment being configured to be secured in said first and second through-holes adjacent said first edge of said base, said threadable segment being configured to be threadable from said first and second through-holes around a vertebra and through said third through-hole adjacent said second edge of said base, said threadable segment being configured to be threadable through said at least one channel imparted transversely through said coupling member, said threadable segment being configured to be tensioned to bring said base into tensioned contact with a vertebra, said lock screw being configured to secure said threadable segment in its tensioned configuration against a wall of said at least one channel imparted transversely through said coupling member.

6. An attachment device for securing to a vertebra, the device comprising a head segment with sidewalls surrounding a hollow vertical core wherein an interior of said sidewalls is threaded, said interior sidewall threads engaging with a threaded lock nut, said lock nut threading into said hollow vertical core;

a base comprising a planar bottom surface, said base being coupled to said head segment, said base including at least one channel imparted through said base, said at least one channel having an entry opening and an exit opening; and a flexible threadable segment, said flexible threadable segment being flexibly threadable through said at least one channel, said flexible threadable segment passing through both said entry and exit openings of said at least one channel said flexible threadable segment being configured to non-invasively secure said rod anchor to a surface of a vertebra wherein a tensioning of said flexible threadable segment brings a bottom surface of said base into tensioned contact against a surface of a vertebra.

* * * * *